(12) United States Patent
Leysen et al.

(10) Patent No.: US 6,403,573 B1
(45) Date of Patent: Jun. 11, 2002

(54) COMPOUNDS OF AZETIDINE AND PYRROLIDIN

(75) Inventors: Dirk Leysen, Lommel (BE); Johannes Hubertus Wieringa; Christophorus Louis Eduard Broekkamp, both of Oss (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/870,032

(22) Filed: May 30, 2001

Related U.S. Application Data

(62) Division of application No. 09/622,705, filed on Aug. 21, 2000, now Pat. No. 6,281,243.

(51) Int. Cl.⁷ ................... C07D 205/12; A61K 31/397; A61P 25/24
(52) U.S. Cl. .................... 514/210.01; 548/952
(58) Field of Search ...................... 548/952; 514/210.01

(56) References Cited

U.S. PATENT DOCUMENTS 5,130,309 A   7/1992   Shanklin, Jr. et al.

FOREIGN PATENT DOCUMENTS

| GB | 2 085 427 A | 4/1982 |
| WO | 0 338 331 A | 6/1989 |

Primary Examiner—Floyd D. Higel
Assistant Examiner—Andrea D'Souza Small
(74) Attorney, Agent, or Firm—William M. Blackstone

(57) ABSTRACT

The invention relates to a compound having formula (I) wherein A is an optionally unsaturated 5- or 6-membered ring, which may comprise a heteroatom selected from N,O and S and which may be substituted with oxo or (1–6C) alkyl; $R^1$, $R^2$ and $R^3$ are independently H, (1–6C) alkyl, (1–6C) alkoxy,(1–6C) alkoxy-(1–6C) alkyl, carbo(1–6C) alkoxy or halogen; X is O or S; and n is 1 or 2; or a pharmaceutically acceptable salt thereof, with the exception of 3-(naphth-1-yl-oxy)-pyrrolidin and 3-(5,6,7,8-tetrahydro-napth-1-yl-oxy)-pyrrolidin. The compounds of the invention have antidepressant activity and can be used in treating or preventing serotonin-related diseases.

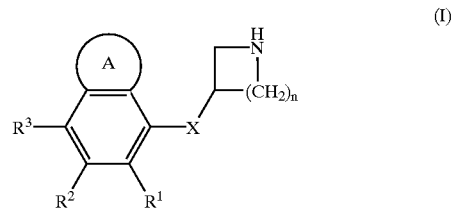

(I)

10 Claims, No Drawings

COMPOUNDS OF AZETIDINE AND PYRROLIDIN

This application is a Division of Ser. No. 09/622,705 Aug. 21, 2000 now U.S. Pat. No. 6,281,243.

The invention relates to derivatives of azetidine and pyrrolidine, to pharmaceutical compositions comprising the same, a process for their preparation, as well as the use of derivatives of azetidine and pyrrolidine for the preparation of a medicament which acts on the central nervous system.

In recent years the contribution of serotonergic activity to the mode of action of antidepressant drugs has been well documented and compounds which enhance activity in the serotonin system have been developed and successfully introduced as antidepressants. Serotonin reuptake inhibitors (SRI) work by increasing the amount of serotonin available at the synapse. Although the SRI's have more favourable side effect profiles than previous generations, they are not devoid of side effects and still suffer from a slow onset of action [Andrews and Nemeroff, "Contemporary management of depression"—American Journal of Medicine 97(6A): 24S–32S (1994); Leonard, "The comparative pharmacology of new antidepressants"—Journal of Clinical Psychiatry 54(Suppl): 3–15 (1993)]. Moreover, the mechanism of action of the SRI's although specific for serotonin, is not selective in that they effect activity at a multitude of different serotonin receptor subtypes. This broad spectrum of activity may lead to many of the side effects associated with the SRI's e.g. nausea from activation of 5-HT3, headache due to activation of 5-HT2B. Thus, SRI's can alter the function of several 5-HT2 receptor subtypes, however, the efficacy of these drugs may correlate most strongly with their effects on the 5-HT2C system [(Broekkamp and Berendsen "The importance of 5-HT1C receptors for anti-depressant effects"—Polish Journal of Pharmacology and Pharmacy 44(Suppl): 20 (1992); Cesana et at "Mesulergine antagonism towards the fluoxetine anti-immobility effect in the forced swimming test in mice"—Journal of Pharmacy and Pharmacology 45: 473–475 (1993); Berendsen and Broekkamp "Comparison of stimulus properties of fluoxetine and 5-HT receptor agonists in a conditioned taste aversion procedure"—European Journal of Pharmacology 253: 83–89 (1994)]. These data suggest that compounds which selectively activate the 5-HT2C receptor will be effective in the treatment of affective disorders and related conditions.

The invention relates to compounds according to the formula I

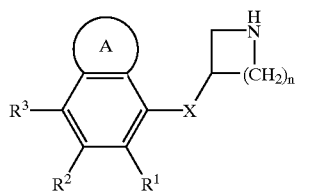

(I)

wherein A is an optionally unsaturated 5- or 6-membered ring, which may comprise a heteroatom selected from N, O and S and which may be substituted with oxo or (1–6C) alkyl; $R^1$, $R^2$ and $R^3$ are independently H. (1–6C) alkyl, (1–6C) alkoxy, (1–6C) alkoxy-(1–6C) alkyl, carbo(1–6C) alkoxy or halogen; X is O or S; and n is 1 or 2; or a pharmaceutically acceptable salt thereof, with the exception of 3-(naphth-1-yl-oxy)-pyrrolidin and 3-(5,6,7,8-tetrahydro-naphth-1-yl-oxy)-pyrrolidin. The compounds have a selective effect on 5-HT2C receptors in the central nervous system.

In U.S. Pat. No. 4,452,809 (filed Apr. 22, 1983) 3-aryloxy-4-hydroxypyrrolidines were disclosed, wherein it was found that 3-naphthyl or 3-indenyloxy-4-hydroxypyrrolidines have antiarrhythmic activity, whereas 3-phenoxy-4-hydroxypyrrolidines were found to have antidepressant activity. Some years earlier, in DT 2,738,477 [priority date Sep. 1, 1977] also 3-aryloxy-4-hydroxypyrrolidines were disclosed, wherein the preferred compounds with antidepressant activity were also 3-phenoxy derivatives. Other 3-aryloxypyrrolidines wherein the pyrrolidine-group of all compounds is N-substituted, having an effect on the serotonin receptor, were disclosed in EP 0,338,331 [priority date Apr. 19, 1988].

Surprisingly, after many years of research, it has now been found, that the compounds of formula I, (bicyclic aryl)oxy-substituted pyrrolidines and (bicyclic aryl)oxy-substituted azetidines wherein the 5- or 4-membered heterocycle is not substituted at any position in the ring, have a selective effect on 5-HT2C receptors in the central nervous system. Also the compounds 3-(naphth-1-yl-oxy)-pyrrolidin and 3-(5,6,7,8-tetrahydro-naphth-1-yl-oxy)-pyrrolidin, known as intermediates but not claimed in EP 0,338,331, were found to have this effect. Therefore, also protection is sought for the use of these compounds and for pharmaceutical compositions comprising them. Thus, the invention also pertains to the first medical use of the compounds according to formula 1, i.e. including the compounds 3-(naphth-1-yl-oxy)-pyrrolidin, 3-(5,6,7,8-tetrahydro-naphth-1-yl-oxy)-pyrrolidin for use as a medicament (or, in other words, for use in therapy).

The use of a selective 5-HT2C agonist ensures that pharmacological activity occurs immediately and preferentially at the 5-HT2C receptors allowing a much quicker onset of selective pharmacological activation than can be observed with SRI's. Moreover the selectivity of the compound reduces the potential for adverse effects mediated by other serotonin receptors e.g. nausea, headache, effects which may hinder compliance and thus interfere with efficacy.

The compounds of the present invention act on the central nervous system, in particular as antidepressants, and against obsessive compulsive disorders, anxiety disorders including generalised anxiety, panic attacks, agoraphobia, eating disorders such as obesity, urinary incontinence, impotence, aggression and drug abuse such as alcohol or narcotic addiction.

Preferred compounds according to the invention have the formula I wherein the heteroatom in A, if present, is N or S; $R^1$ is H, (1–6C) alkyl, (1–6C) alkoxy, (1–6C) alkoxy-(1–6C) alkyl; $R^2$ is H, (1–6C) alkoxy, carbo(1–6C) alkoxy or halogen and $R^3$ is H, (1–6C) alkyl, (1–6C) alkoxy or halogen.

More preferred are compounds of the formula (Ia)

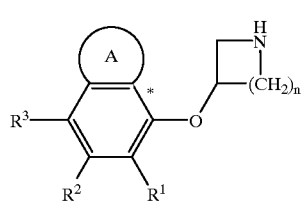

(Ia)

wherein A is an unsubstituted saturated 5-membered or optionally aromatic 6-membered ring, which may comprise a nitrogen atom adjacent to the position indicated with an asterisk; $R^1$ is H or (1–6C) alkoxy; $R^2$ is H, (1–6C) alkoxy or halogen; $R^3$ is H or halogen; and n is 1 or 2. More preferred are the compounds of formula (Ia) wherein A is an unsubstituted saturated 5-membered or optionally aromatic 6-membered ring; $R^1$ is (1–6C) alkoxy and $R^2$ and $R^3$ are H. Most preferably, A in formula (Ia) is a 5-membered ring and $R^1$ is methoxy, in particular when n is 2.

The term (1–6C) alkyl means a branched or unbranched alkyl group having 1 to 6 carbon atoms, such as methyl, ethyl, t-butyl, isopentyl, and the like. The most preferred alkyl group is methyl.

The term (1–6C) alkoxy means an alkoxy group having 1–6 carbon atoms, the alkyl moiety of which having the meaning as previously defined. The most preferred alkoxy group is methoxy.

The term halogen means fluorine, chlorine or bromine.

The compounds according to formula I may be prepared in a manner conventional for such compounds. To that end, compounds of general formula II, wherein A, R¹, R2, R³, X and n are as previously defined and P is any N-protecting group, stable under alkaline conditions [suitable N-protecting groups can be found in T. W. Green and P. G. M. Wuts: Protective Groups in Organic Synthesis, Second Edition (Wiley, N.Y., 1991)], are deprotected using the appropriate conditions such as catalytic hydrogenation or intermediate carbamate formation, followed by reaction with alcohols. Optionally at the same time, a salt may be formed.

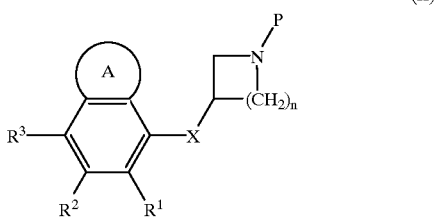

(II)

The compounds according to general formula II may be prepared by arylether formation of suitable N-protected 3-hydroxy-azetidines or -pyrrolidines, wherein the protecting group is as hereinbefore defined, with appropriately substituted aromatic or heteroaromatic compounds bearing a suitable leaving group. Alternatively, N-protected-azetidines or -pyrrolidines bearing a suitable leaving group at the 3-position, such as halogen, triflate, tosylate or mesylate, can be reacted with appropriately substituted aromatic or heteroaromatic compounds bearing a hydroxy, or mercapto group.

The compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, ascorbic acid and the like.

The compounds of this invention may possess one or more chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns.

The compounds of the invention may be administered enterally or parenterally, and for humans preferably in a daily dosage of 0.001–100 mg per kg body weight, preferably 0.01–10 mg per kg body weight. Mixed with pharmaceutically suitable auxiliaries, e.g. as described in the standard reference, Gennaro et at., Remington's Pharmaceutical Sciences, (18th ed., Mack Publishing Company, 1990, see especially Part 8: Pharmaceutical Preparations and Their Manufacture) the compounds may be compressed into solid dosage units, such as pins, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray. For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

EXAMPLES

EXPERIMENTAL

GENERAL METHODS

A first general process step consists of the preparation of a suitable N-protected-3-hydroxy-azetidine and -pyrrolidine and subsequent aryether formation.

Any protective group, stable under alkaline coupling conditions will do. This applies also for the pyrrolidines series, where a benzyl group is found to be the best accessible and most convenient protective group. As for the azetidines a bulky group such as triphenylmethyl, 4,4'-disubstituted diphenylmethyl, α-methylbenzyl and, as a matter of choice, diphenylmethyl can be used for the ease of azetidine ring formation during synthesis. These compounds may be prepared by reacting the corresponding primary amines with epichlorohydrine in a polar solvent such as methanol or dimethylformamide at elevated temperatures ranging from room a temperature to reflux, usually over a period of several days.

The N-protected-3-hydroxy-azetidines and -pyrrolidines can be used as such in a condensation reaction with a wide variety of compounds bearing a suitable leaving group on an aromatic moiety to get ether formation. When the leaving group is for instance halogen the reaction can be performed in a polar solvent such as dimethylformamide and a suitable base, for example potassium carbonate in the presence of a catalyst like activated copper, at elevated temperatures ranging from room temperature up to reflux temperature.

In a preferred second general process step the hydroxy group of the N-protected-3-hydroxy-azetidines and -pyrrolidines is converted, by methods well known to a skilled person, into a reactive leaving group such as for instance halogen, triflate, tosylate and, for choice, mesylate, followed by a condensation reaction with a wide variety of compounds bearing an aromatic hydroxy (or mercapto) group to get a wide variety of aryl ethers, as well as aryl thioethers.

The mesylates are conveniently prepared by the addition of methanesulfonylchloride to the 3-hydroxy compounds in an apolar solvent such as toluene in the presence of an organic base like triethylamine at a temperature of −30° C. up to reflux temperature, usually at reduced temperature.

Although all common aryl-alkyl ether formation reactions known from literature may be applicable, most compounds were prepared according to three main procedures.

(I) A first general applicable preparation consist of a heterogeneous two phase reaction between mesylate and an appropriate nucleophile, preferably a bicyclic compound containing an aromatic hydroxy or mercapto group. The two phase system consists of an aqueous solution of an inorganic base such as sodium hydroxide and an organic layer, preferably 4-methyl-2-pentanone. The reaction is performed at a temperature of 25° C. up to reflux temperature, preferably at elevated temperature.

(ii) A second preparation consists of a condensation reaction of both substrates, mesylate and nucleophile, in a polar organic solvent such as tert-butanol or dimethylsulfoxide or mixtures thereof and a suitable base like potassium tert-butoxide, generally at elevated temperatures ranging from 25° C. up to 100° C.

iii) A third preparation consists of anion formation by a base like sodium hydride and subsequent reaction with mesylate in a polar solvent such as dimethylformamide, usually at elevated temperatures ranging from 25° C. up to reflux.

A third general process step concerns all types of deprotection methods resulting in (cyclic) secondary amines. All convential methods with regard to the selected protective group, well known to a skilled person, must be taken in consideration As for the aralkyl groups commonly used in this invention two types of deprotection methods are preferred. The first method consists of the removal of the protective group by catalytic hydrogenation at a pressure varying from atmospheric to 60 psi in a polar solvent such as ethanol or methanol in the presence of a commonly used catalyst such as palladium on activated carbon or palladium hydroxide on carbon at a temperature of 25–60° C. A second method consist of the replacement of the original protective group by an intermediate carbamate function which on turn is removed afterwards. Suitable reagents are for instance 1-chloroethyl chloroformate or vinyl chloroformate in an aprotic solvent such as 1,2-dichloroethane at a temperature of −15° C. up to reflux temperature and subsequent reaction with an alcohol such as methanol or ethanol at a temperature of −15° C. up to reflux temperature.

A fourth general process step concerns the preparation or separation of stereoisomers, including diastereomers and enantiomers, as a consequence of the presence of one or more centres of chirality.

Enantio selective preparations can be performed starting from enantio pure (R) and (S) substrates such as for instance (R)- or (S)-1-benzyl-3-pyrrolidinol.

The individual enantiomers may also be obtained from a mixture of stereoisomers using any method well known in the art for separating such isomers into their constituent enantiomers. For example, using methods described in Stereochemistry of Organic compounds, E. L. Eliel and S. H. Wilen, chapter 7, 1994. In particular by methods such as salt formation with optically active acids followed by fractional crystallisation or by differential absorption using columns packed with chiral material, for example chiral liquid or gas chromatography.

A fifth general process step includes the conversion of the secondary and tertiary amines prepared during synthesis into any salt or solvate form, preferably pharmaceutically accepted salts and solvates such as hydrochloride salts, namely prepared by addition of the acid of choice to the free base in a solvent like ethanol and isolation as a solid.

PREPARATION OF STARTING MATERIALS
(azetidine substrates)

Smooth procedure suitable for large scale production of both 1-(diphenylmethyl)-3-azetidinol and its methanesulfonate (modification of U.S. Pat. No. 4,183,923 E. H. Gold et. al. January 1980):

1-(Diphenylmethyl)-3-azetidinol

Under nitrogen diphenylmethylamine (34.5 ml) was added to a solution of epichlorohydrine (34.7 ml) in 1L of anhydrous dimethylformamide. The reaction mixture was heated at 95° C. for 64 hours. Afterwards it was cooled to 5° C. and a mixture of 20 ml of concentrated aqueous hydrochloric acid and 20 ml of water was added dropwise. After evaporation in vacuo the residue was stirred with diethyl ether and filtered. The solid was washed with diethyl ether and then partitioned between diethyl ether and a 2N aqueous sodium hydroxyde solution. The organic layer was dried over sodium sulfate, filtered and concentrated in vacuo. The residue was crystallized from a mixture of toluene and petrol ether to give 36.3 g of 1-(diphenylmethyl)-3-azetidinol, mp. 107° C.

1-(Diphenylmethyl)-3-methanesulfonyloxy-azetidine

Under nitrogen methanesulfonylchloride (7.8 ml) was dropped slowly into a suspension of 1-(diphenylmethyl)-3-azetidinol (29.3 g) and triethylamine (14 ml) in 220 ml of dry toluene at a temperature of 15° C. The temperature was allowed to raise to room temperature slowly and the reaction mixture was stirred for 17 hours. Then 220 ml of dry diethyl ether were added and the precipitated triethylamine hydrochloride was filtered and washed with a diethyl ether/dichloromethane mixture (4:1). The organic layer was washed with 100 ml of a 1.1M sodium bicarbonate solution and then with brine. It was dried over sodium sulfate filtered and evaporated in vacuo to give 29.4 g of 1-(diphenylmethyl)-3-methanesulfonyloxy-azetidine, M.S. (C.I.) (M/Z): 318 [M+H]$^+$.

PREPARATION OF OTHER STARTING MATERIALS

5-Chloro-2,3-dihydro-1H-inden-4ol (Step a, b, c)
a) 3-Chloro-propanoic Acid 2-Chlorophenyl Ester 3-chloropropionylchloride (14 ml) was added to 2-chlorophenol (18.18 g) and the mixture was stirred and heated at 60° C. for 1 hour, at 75° C. for 1 hour and left over the weekend at ambient temperature. The compound was purified by destillation in vacuo to give 19,7 g (b.p. 91–94° C. 0.08 mm Hg) of 3-chloro-propanoic acid 2-chlorophenyl ester.

b) 6-Chloro-2,3-dihydro-7-hydroxy-1H-inden-1-one

To 3-chloro-propanoic acid 2-chlorophenyl ester (19.6 g) was added 1 equivalent of aluminum chloride (11.93 g) and the mixture was stirred under nitrogen for 2.5 hours at 100° C., cooled, a second portion of aluminum chloride (14 g) added, and heated at 170° C. for 2 hours.

The reaction mixture was cooled to 70–80° C. and water was added carefully. Then ethyl acetate was added while stirring and the layers separated. The ethyl acetate solution was washed with water, dried over magnesium sulfate, filtered and concentrated in vacuo. A solid separated which was removed by filtration and the remaining filtrate was evaporated until dryness. The residue was chromatographated over silica using toluene as the eluent giving 3.2 g of 6-chloro-2,3-dihydro-7-hydroxy-1H-inden-1-one, M.S. (C.I.) (M/Z): 183 [M+H]$^+$.

c) 5-Chloro-2,3-dihydro-1H-inden-4-ol 3.2 g of 6-chloro-7-hydroxy-1H-inden-1-one in 16.8 ml of water and 67.2 ml of concentrated aqueous hydrochloric acid were stirred and heated with freshly prepared zinc amalgame (from 26.88 g of zinc wool) in an oil bath at 120° C. for 16 hours. The reaction mixture was cooled, decanted and treated with ethylacetate and dichloromethane. The organic layer was evaporated in vacuo. The residue was purified by an acid/base separation yielding 2.08 g of 5-chloro-2,3-dihydro-1H-inden-4-ol, M.S. (C.I.) (M/Z): 169 [M+H]$^+$.

In an analogues manner 2,3-Dihydro-5-methyl-1H-inden-4-ol, M S. (C.I.) (M/Z): 149 [M+H]$^+$ was prepared, starting from 3-chloro-propanoic acid 2-methylphenyl ester.

2.3-Dihydro-5-methoxy-1H-inden-4-ol (Step a, b, c, d) ps a) 3-(2,3-Dimethoxyphenyl)-propanoic Acid Nitrogen was passed through a stirred suspension of (Z)-3-(2,3-dimethoxyphenyl)-2-propenoic acid (14,67 g) in 400 ml of methanol during 15 minutes. Then 1.4 g of 10% palladium on activated carbon were added and a stream of hydrogen was passed through the reaction mixture for 16 hours. After removing the palladium catalyst by filtration, the filtrate was evaporated to yield 14.2 g of 3-(2,3-dimethoxyphenyl)-propanoic acid, M.S. (C.I.) (MZ): 211 [M+H]$^+$.

b) 2,3-Dihydro-4,5-dimethoxy-1H-inden-1-one

Under nitrogen a solution of 3-(2,3-dimethoxyphenyl)-propanoic acid (2 g) in 50 ml methanesulfonic acid was warmed at 60° C. and kept there for 2 hours. The reaction mixture was cooled to room temperature and poured into ice/water. After extraction with ethyl acetate the organic layer was washed with a 1N aqueous sodium hydroxyde solution, dried over magnesium sulfate, filtered and evaporated in vacuo yielding 1.2 g of 2,3-dihydro4,5-dimethoxy-1H-inden-1-one, M.S. (C.I.) (M/Z): 193 [M+H]$^+$.

c) 2,3-Dihydro4-hydroxy-5-methoxy-1H-inden-1-one

Under a nitrogen atmosphere 2,3-dihydro-4,5-dimethoxy-1H-inden-1-one (31.7 g) was dissolved in 600 ml of anhydrous 1,2-dichloroethane and cooled to 0° C. Aluminum chloride (44 g) was added in portions and the reaction mixture was heated to 60° C. for 17 hours, cooled to room temperature and poured into ice/water. After extraction with dichloromethane the organic layer was dried and evaporated. The residue was crystallized from ethyl acetate to give 20.5 g of 2,3-dihydro-4-hydroxy-5-methoxy-1H-inden-1-one, M.S. (C.I.) (M/Z): 179 [M+H]$^+$.

d) 2,3-Dihydro-5-methoxy-1H-inden-4-ol

The 20.5 g of 2,3-dihydro4-hydroxy-5-methoxy-1H-inden-1-one were suspended in a mixture of 310 ml of concentrated aqueous hydrochloric acid and 53 ml of water. Freshly prepared zinc amalgame (from 87 g of zinc wool) was added and the mixture was stirred for 3 hours at ambient temperature. After decantation the resting zinc amalgame was washed three times with diethyl ether and the acidic water solution was extracted with diethyl ether. The combined ether solutions were washed with a 1N aqueous hydrochloric acid solution, dried over magnesium sulfate, filtered and evaporated in vacuo to afford 15.0 g of 2,3-dihydro-5-methoxy-1H-inden-4-ol, M.S. (C.I.) (M/Z): 165 [M+H]$^+$.

6-Fluoro-1-methyl-1H-inden-4-ol (Step a, b, c)

a) 4-Chloro-butanoic Acid 3-fluorophenyl Ester

4-Chlorobutyrylchloride (35.3 g) was added to 3-fluorophenol (25 g). This mixture was stirred during 48 h at room temperature. After the reaction was completed the product was purified by vacuo-destillation. Yield: 35,3 g (b.p. 106° C. 3 mmHg) of 4-chloro-butanoic acid 3-fluorophenyl ester as a white oil.

b) 5-Fluoro-2,3-dihydro-7-hydroxy-3-methyl-1H-inden-1-one

After the obtained 4-chloro-butanoic acid 3-fluorophenyl ester (35.33 g) was heated to 80° C., aluminium chloride (24.0 g) was added. The reaction mixture started to foam. After the foaming was reduced the mixture was stirred during 2 hours at 100° C. After cooling water and ethyl acetate were added and the mixture was heated on a steam bath After all the oil was dissolved the organic layer was separated and washed with water and brine. The solvent was removed and the residue was crystallized from 2-propanol to give 21.2 g of 5-fluoro-2,3-dihydro-7-hydroxy-3-methyl-1H-inden-1-one, M.S. (C.I.) (M/Z): 181 [M+H]$^+$.

c) 6-Fluoro-2,3-dihydro-1-methyl-1H-inden-4-ol 5 g of 5-fluoro-2,3-dihydro-7-hydroxy-3-methyl-1H-inden-1-one was heated to 80° C. until all the solid was melted. After adding aluminium chloride (9.3 g) to this melt the reaction mixture was heated to 170° C. during 17 hours. After cooling water and ethyl acetate were added and the mixture was heated on a steam bath until everything was dissolved. The organic layer was separated and washed with water and brine. After removing the solvent the compound was purified by chromatography with the add of heptane/ethylacetate (9:1) resulting in 2.2 g of 6-fluoro-2,3-dihydro-1-methyl-1H-inden-4-ol as a semi-solid, M.S. (C.I.) (M/Z): 167 [M+H]$^+$.

PREPARATIONS

Example 1

3-[(5-Chloro-2,3-dihydro-1H-inden-4-yl)oxy]-1-(diphenylmethyl)-azetidine a) 2 g of 5-chloro-2,3-dihydro-1H-inden-4-ol were stirred in 75 ml of a 2N sodium hydroxyde solution for 1 hour. To the clear solution were added 75 ml of 4-methyl-2-pentanone and 3.76 g of 1-(diphenylmethyl)-3-methanesulfonyloxy-azetidine and the mixture was heated in an oil bath at 120° C. for 3.5 hours. Then another 2 g of mesylate were added and heating was continued for 64 hours. The upper layer was separated and washed with water. Evaporation in vacuo and chromatography with toluene/ethyl acetate (95:5) gave 4.22 g of 3-[(5-chloro-2,3-dihydro-1H-inden-4-yl)oxy]-1-(diphenylmethyl )-azetidine as a clear oil that solidified spontaneous. M.S. (C.I.) (M/Z): 391 [M+H]$^+$.

In a similar way were prepared:

b) 3-[(2,4-Dichloro-1-naphtalenyl)oxy]-1-(diphenylmethyl)-azetidine, M.S. (C.I.) M/Z): 435 [M+H]$^+$, starting from 2,4-dichloro-1-naphtol, 1-(Diphenylmethyl)-3-[(4-methyl-1-naphtalenyl)oxy]-azetidine, M.S. (C.I.) (M/Z): 380 [M+H]$^+$, starting from 4-methyl-1-naphtol, d) 1-(Diphenylmethyl)-3-[(2-methoxy-1-naphtalenyl)oxy]-azetidine, M.S. (C.I.) (M/Z):396 [M+H]$^+$, starting from 2-methoxy-1-naphtol, e) 1-(Diphenylmethyl)-3-[(5,6,7,8-tetrahydro-1-naphtalenyl)oxy]-azetidine, M.S.(C.I.) M/Z): 370 [M+H]$^+$, starting from 5,6,7,8-tetrahydro-1-naphtol, 1-(Diphenylmethyl)-3-[(2,3-dihydro-5-methoxy-1H-inden-4-yl)oxy]-azetidine, M.S. (C.I.) (M/Z): 386 [M+H]$^+$, starting from 2,3-dihydro-5-methoxy-1H-inden-4-ol, g) 3-[(7-Bromo-2,3-dihydro-1H-inden-4-yl)oxy]-1-(diphenylmethyl)-azetidine, M.S. (C.I.) (M/Z): 435 [M+H]$^+$, starting from 7-bromo-2,3-dihydro-1H-inden-4ol, h) 1-(Diphenylmethyl)-3-[(6-fluoro-2,3-dihydro-1-methyl-1H-inden-4-yl)oxy]-azetidine, M.S. (C.I.) (M/Z): 388 [M+H]$^+$, starting from 6-fluoro-2,3-dihydro-1-methyl-1H-inden-4-ol, i) 3-[(2,3-Dihydro-5-methyl-1H-inden-4-yl)oxy]-1-(diphenylmethyl)-azetidine, M.S. (C.I.) (M/Z): 370 [M+H]$^+$, starting from 2,3-dihydro-5-methyl-1H-inden-4-ol, j) 1-(Diphenylmethyl)-3-[(2,3-dihydro-1H-inden-4-yl)oxy]-azetidine, M.S. (C.I.) (M/Z): 356 [M+H]$^+$, starting from 2,3-dihydro-1H-inden-4-ol, k) 3-[(Benzo(b)thien 4yl)1-(diphenylmethyl)-azetidine, M.S. (C.I.) (M/Z): 372 [M+H]$^+$, starting from benzo (b)thiophene4-ol, l) 5-(3-Azetidinyloxy)-1-(diphenylmethyl)-isoquinoline, M.S. (C.I.) (M/Z): 367 [M+H]⁺, starting from 5-hydroxyisoquinoline, m) 8-(3-Azetidinyloxy)-1-(diphenylmethyl)-quinoline, M.S. (C.I.) (M/Z): 371 [M+H]⁺, starting from 8-hydroxyquinoline.

Example 2

1-(Diphenylmethyl)-3-(1-naphtalenyloxy)-azetidine Hydrochloride a) Under nitrogen 1.44 g of 1-naphtol were added to a solution of 3.37 g of potassium tert-butoxide in 71 ml tert-butanol. After stirring for half an hour 4.33 g of 1-(diphenylmethyl)-3-methancsulfonyloxy-azetidine maleate were added. To increase the solubility 71 ml of dimethyl sulfoxide were added. The mixture was heated in an oil bath at 80° C. for 40 hours. t-Butanol was distilled off in vacuo and the residue partitioned between water and ethyl acetate. The ethyl acetate extracts were washed with water, dried over magnesium sulfate, filtered and evaporated in vacuo. The residue was chromatographated with toluene giving 2.7 g of the desired product. This was treated with a solution of hydrochloric acid in methanol, evaporated in vacuo and crystallized from ethanol absolute, yielding 2.09 g of 1-(diphenylmethyl)-3-(1-naphtalenyloxy)-azetidine hydrochloride, m.p. 182° C.

In a similar way were prepared:

b) 1-(Diphenylmethyl)-3-[(2-methyl-1-naphthalenyl)oxy]-azetidine, M.S. (C.I.) (M/Z): 380 [M+H]⁺, starting from 2-methyl-1-naphtol, c) 1-(Diphenylmethyl)3-[(4-methoxy-1-naphthalenyl)oxy]-azetidine, M.S. (C.I.) M/Z): 396 [M+H]⁺, starting from 4-methoxy-1-naphthol, d) 1-(Diphenylmethyl)-3-(1-naphthalenylthio)-azetidine, M.S. (C.I.) (M/Z): 382 [M+H]⁺, starting from 1-naphthalenethiol, e) 1-(Diphenylmethyl)-3-(2-naphtalenyloxy)-azetidine, M.S. (C.I.) (M/Z): 366 [M+H]⁺, starting from 2-naphthol.

Example 3

1-(Diphenylmethyl)-3-[(2-methoxy-1-naphthalenyl)oxy]-azetidine Hydrochloride a) A stirred mixture of 6.89 g of 1-(diphenylmethyl)-3-azetidinol, 25 ml anhydrous dimethyl formamide, 10.37 g potassium carbonate, 5.93 g 1-bromo-2-methoxynaphtalene and 200 mg of activated copper was heated for 40 hours in an oil bath of 170° C. The reaction mixture was partitioned between water and toluene. The crude product mixture from the organic extracts was chromatographated with toluene and toluene/ethyl acetate (95:5). The desired product was dissolved in diethyl ether and precipitated by the addition of a solution of hydrochloric acid in methanol. Yield: 1.96 g of 1-(diphenylmethyl)-3-[(2-methoxy-1-naphtalenyl)oxy]-azetidine, M.S. (C.I.) (M/Z): 400 [M+H]⁺.

In a similar way was prepared:

b) 1-(Diphenylmethyl)-3-[(2-(methoxymethyl)-1-naphthalenyl)oxy]-azetidine hydrochloride, M.S. (C.I.) (M/Z): 410 [M+H]⁺, starting from 1-bromo-2-(methoxymethyl)-naphthalene.

Example 4

3-[(2,3-Dihydro-1H-inden-4-yl)oxy]-azetidine Hydrochloride a) To a suspension of 3 g of 3-[(2,3-dihydro-1H-inden-4yl)oxy]-1-(diphenylmethyl)-azetidine hydrochloride in 250 ml ethanol were added 600 mg of palladium hydroxyde on carbon powder and the mixture was hydrogenated in a Parr apparatus at 60 psi during 16 hours. After removal of the catalyst and evaporation of the solvent in vacuo the residue was washed several times with diethyl ether and decanted to remove the diphenylmethane formed. The remaining solid was crystallized from ethanol/diethyl ether, yielding 1.27 g of 3-[(2,3-dihydro-1H-inden-4-yl)oxy]-azetidine hydrochloride, m.p. 65° C.

In a similar way were prepared:

b) 3-[(2-Methyl-1-naphthalenyl)oxy]-azetidine hydrochloride, mp 171° C. starting from 1-(diphenylmethyl)-3-[(2-methyl-1-naphtalenyl)oxy]-azetidine, c) 3-(1-Naphthalenyloxy)-azetidine hydrochloride, mp 292° C. starting from 1-(diphenylmethyl)-3-[(1-naphtalenyl)oxy]-azetidine, d) 3-[(4-Methoxy-1-naphthalenyl)oxy]-azetidine hydrochloride, mp 198° C. starting from 1-(diphenylmethyl)-3-[(4-methoxy-1-naphtalenyl)oxy]-azetidine, e) 3-[(5,6,7,8-Tetrahydro-1-naphthalenyl)oxy]-azetidine hydrochloride, mp 187° C. starting from 1-(diphenylmethyl)-3-[(5,6,7,8-tetrahydro-1-naphtalenyl)oxy]-azetidine, f) 3-[(5,6,7,8-Tetrahydro-2-methoxy-1-naphthalenyl)oxy]-azetidine hydrochloride, mp 164° C. starting from 1-(diphenylmethyl)-3-[(2-methoxy-1-naphtalenyl)oxy]-azetidine, g) 3-(2-Naphthalenyloxy)-azetidine hydrochloride, mp 168° C. starting from 1-(diphenylmethyl)-3-(2-naphtalenyloxy)-azetidine h) 8-(3-Azetidinyloxy)-1,2,3,4-tetrahydroquinoline hydrochloride, mp >250° C. starting from 8-(3-Azetidinyloxy)-1-(diphenylmethyl)-quinoline.

Example 5

3-[(5-Chloro-2,3-dihydro-1H-inden-4-yl)oxy]-azetidine Hydrochloride a) 4.22 g of 3-[(5-chloro-2,3-dihydro-1H-inden-4-yl)oxy]-1-((diphenylmethyl))-azetidine were dissolved in 71 ml of 1,2-dichloroethane. 1.58 g of 1-chloroethyl chloroformate was added. The mixture was refluxed in an oil bath at 120° C. for 2.5 hours. After evaporation in vacuo the residue was refluxed in 71 ml of anhydrous methanol for 2 hours. Evaporation in vacuo gave a semi solid that was stirred with diethyl ether and filtered. The solid was recrystallized from ethanol/diethyl ether, yielding 1.57 g of 3-[(5-chloro-2,3-dihydro-1H-inden-4-yl)oxy]-azetidine hydrochloride, mp. 188° C.

In a similar way were prepared:

b) 3-[(2,4-Dichloro-1-naphthalenyl)oxy]-azetidine hydrochloride, mp 187° C. starting from 3-[(2,4-Dichloro-1-naphtalenyl)oxy]-1-(diphenylmethyl)-azetidine, c) 3-[(4-Methyl-1-naphthalenyl)oxy)-azetidine hydrochloride, mp 180° C. starting from 1-(diphenylmethyl)-3-[(4-methyl-1-naphtalenyl)oxy]-azetidine, d) 3-[(2,3-Dihydro-5-methoxy-1H-inden-4-yl)oxy]-azetidine hydrochloride, mp 166° C. starting from 1-(diphenylmethyl)-3-[(2,3-dihydro-5-methoxy-1H-inden-4-yl)oxy]-azetidine, e) 3-[(7-Bromo-2,3-dihydro-1H-inden-4-yl)ox]-azetidine hydrochloride, mp 203° C. starting from 3-[(7-bromo-2,3-dihydro-1H-inden-4-yl)oxy]-1-(diphenylmethyl)-azetidine, f) 3-[(6-Fluoro-2,3-dihydro-1-methyl-1H-inden-4-yl)oxy]-azetidine hydrochloride, mp 170 ° starting from 1-(diphenylmethyl)-3-[(6-fluoro-2,3-dihydro-1-methyl-1H-inden4-yl)oxy]-azetidine, g) 3-[(2,3-Dihydro-5-methyl-1-H-inden-4-yl)oxy]-azetidine hydrochloride mp 184° C. starting from 1-(diphenylmethyl)-3-[(2,3-dihydro-5-methyl-1-H-inden-4-yl)oxy]-azetidine, h) 3-[(Benzo[b]thien4-yl)oxy]-azetidine hydrochloride, mp 203° C. starting from 3-[(benzo[b]thien4-yl)oxy]-1-(diphenylmethyl)-azetidine, i) 5-(3-Azetidinyloxy)-isoquinoline dihydrochloride, mp 198° C. starting from 5-(3-azetidinyloxy)-1-(diphenylmethyl)-isoquinoline.

Example 6

3-[(2-Methoxy-1-naphthalenyl)oxy]-azetidine Hydrochloride a) To a solution of 2.07 g of 1-(diphenylmethyl)-3-[(2-methoxy-1-naphtalenyl) oxy]-azetidine as that free base in 20 ml 1,2-dichloroethane at −15° C. was added dropwise a solution of 0.58 ml vinyloxy carbonylchloride in 20 ml 1,2-dichloroethane over 15 minutes and the reaction was kept at this temperature for another half hour. After 16 hours at ambient temperature ethanol was added from a dropping funnel. The reaction mixture was evaporated in vacuo and the residue was purified by chromatography using toluene/ethyl acetate (95:5) to afford 1.55 g of a solid which was dissolved in 25 ml of a 2M hydrochloric acid/methanol solution. After standing at ambient temperature for 16 hours the solution was evaporated in vacuo and the product crystallized from ethanol/diethyl ether. Isolated 1.02 g of 3-[(2-methoxy-1-naphtalenyl)oxy]-azetidine hydrochloride m.p. 187° C.

In a similar way were prepared:

b) 3-(1-Naphthalenylthio)-azetidine hydrochloride, mp 159° C. starting from 1-(diphenylmethyl)-3-(1-naphtalenylthio)-azetidine, c) 3-[(2-(Methoxymethyl)-1-naphtalenyl)oxy]-azetidine hydrochloride, mp 127° C. starting from 1-(diphenylmethyl)-3-[(2-(methoxymethyl)-1-naphtalenyl)oxy]-azetidine.

Example 7

(R)-3-Methanesulfonyloxy-1-(phenylmethyl)-pyrrolidine a) 10 g of (R)-1-(phenylmethyl)-3-pyrrolidinol were dissolved in 160 ml of anhydrous toluene. The solution was stirred under a stream of nitrogen, cooled in an ice/ethanol bath and 8.7 ml of triethylamine were added. At a temperature of −5° C. 4,9 ml of a solution of methanesulfonylchloride in 110 ml of anhydrous toluene were added dropwise over 1,5 hours and the reaction mixture was stirred for 1 hour at 0° C. The solid was filtered and washed with ethyl acetate. The filtrate was washed with water, dried and evaporated in vacuo to give 13,9 g of (R)-3-methanesulfonyloxy-1-(phenylmethyl)-pyrrolidine as an almost colourless oil. M.S. (C.I.) (M/Z): 256 [M+H]$^+$.

In a similar way were prepared:

b) (S)-3-methanesulfonyloxy-1-(phenylmethyl)-pyrrolidine, M.S. (C.I.) (M/Z): 256 [M+H]$^+$, starting from (S)-1-(phenylmethyl)-3-pyrrolidinol, c) (rac)-3-methanesulfonyloxy-1-(phenylmethyl)-pyrrolidine, M.S. (C.I) (M/Z): 256 [M+H]$^+$, starting from (rac)-1-(phenylmethyl)-3-pyrrolidinol.

Example 8

(S)-3-[(2,3-Dihydro-5-methoxy-1H-inden-4-yl)oxy]-1-(phenylmethyl)-pyrrolidine a) In 540 ml of anhydrous dimethylformamide 5 g of 2,3-dihydro-5-methoxy-1H-inden-4-ol were dissolved. The solution was stirred, placed under a steam of nitrogen and 1.5 g of a 60% dispersion of sodium hydride in oil was added. The reaction mixture was stirred at room temperature for half an hour. The temperature was raised to 100° C. and a solution of 7.78 g of (R)-3-methanesulfonyloxy-1-(phenylmethyl)-pyrrolidine in 78 ml of anhydrous dimethylformamide was added dropwise over 1 hour. Another 3,0 g of mesylate in 30 ml of anhydrous dimethylformamide were added dropwise over 0.5 hours and the reaction continued for another 1.5 hours at 100° C. Evaporation in vacuo gave a semi solid that was partitioned between water and ethyl acetate. The ethyl acetate extract was dried and evaporated in vacuo. The derived product was isolated by chromatography over silica using toluene/-ethanol as the eluent giving 9.45g of (S)-3-[(2,3-dihydro-5-methoxy-1H-inden-4-yl)oxy]-1-(phenylmethyl)-pyrrolidine as an oil. M.S. (C.I.) (M/Z): 324 [M+H]$^+$.

In a similar way were prepared b) (R)-3-[(2,3-dihydro-5-methoxy-1H-inden-4-yl)oxy]-1-(phenylmethyl)-pyrrolidine, M.S. (C.I.) (M/Z): 324 [M+H]$^+$, starting from 2,3-dihydro-5-methoxy-1H-inden-4-ol and (S)-3-methanesulfonyloxy-1-(phenylmethyl)-pyrrolidine, c) (rac)-3-[(2,3-Dihydro-5-methoxy-1H-inden-4-yl)oxy]-1-(phenylmethyl-pyrrolidine M.S. (C.I.) (M/Z):324 [M+H]$^+$, starting from 2,3-dihydro-5-methoxy-1H-inden-4-ol and (rac)-3-methanesulfonyloxy-1-(phenylmethyl)-pyrrolidine, d) 3-(1-Naphthalenyloxy)-1-(phenylmethyl)-pyrrolidine M.S. (C.I.) (M/Z): 304 [M+H]$^+$, starting from 1-naphtol, e) 3-[(5,6,7,8-Tetrahydro-1-naphthalenyl)oxy]-1-(phenylmethyl)-pyrrolidine, M.S. (C.I.) (M/Z): 308 [M+H]$^+$, starting from 5,6,7,8-tetrahydro-1-naphthol.

Example 9

(S)-(+)-3-[(2,3-Dihydro-5-methoxy-1H-inden-4-yl)oxy]-pyrrolidine Hydrochloride a) 9.4 g of (S)-3-[(2,3-dihydro-5-methoxy-1H-inden-4yl)oxy]-1-(phenylmethyl)-pyrrolidine were dissolved in 300 ml of anhydrous methanol and 2,0 g of palladium hydroxyde on carbon added. The mixture was hydrogenated in a Parr apparatus for 16 hours at 50 psi. The catalyst was filtered over dicalite and washed with methanol. The filtrate was concentrated to its original volume and 1 g of fresh palladium hydroxide or carbon was added. Hydrogenation was continued for 3 hours. The catalyst was removed again and the filtrate treated with excess of a 1M hydrochloric acid/diethyl ether solution Evaporation and crystallization form methanol/ethyl acetate/diethyl ether gave coloured crystals that where washed with acetone and diethyl ether giving 3,95 g of (S)-(+)-3-[(2,3-dihydro-5-methoxy-1H-inden-4-yl)oxy]-pyrrolidine hydrochloride, m.p. 176° C.

In a similar way was prepared:

b) 3-[(5,6,7,8-Tetrahydro-1-naphthalenyl)oxy]-pyrrolidine hydrochloride m.p. 207° C., starting from 3-[(5,6,7,8-tetrahydro-1-naphthalenyl)oxy]-1-(phenylmethyl)-pyrrolidine Example 10

(R)-(−)-3-[(2,3-Dihydro-5-methoxy-1H-inden-4-yl)oxy]-pyrrolidine Hydrochloride a) 800 mg of (R)-3-[(2,3-dihydro-5-methoxy-1H-inden-4-yl)oxy]-1-(phenylmethyl)-pyrrolidine were dissolved in 150 ml of anhydrous methanol and 1.5 equivalent of hydrochlorid acid solved in ethyl acetate was added. Approximately 80 mg of palladium on carbon 10% were added and a stream of hydrogen was passed through the stirred mixture. After 24 hours new catalyst was added and hydrogenation continued for 17 hours. The catalyst was removed by filtration, the filtrate evaporated in vacuo and the product crystallized from ethanol/ethyl acetate/diethyl ether yielding 360 mg of (R)-(−)-3-[(2,3-dihydro-5-methoxy-1H-inden-4-yl)oxy]-pyrrolidine hydrochloride mp. 174° C.

In a similar way were prepared:

b) (rac)-3-[(2,3-Dihydro-5-methoxy-1H-inden-4-yl)oxy]pyrrolidine hydrochloride m.p. 154° C., starting from (rac)-3-[(2,3-dihydro-5-methoxy-1H-inden-4yl)oxy]-1-(phenylmethyl) pyrrolidine, c) (rac)-3-[(1-Naphtalenyl)oxy]pyrrolidine hydrochloride m.p. 222° C., starting from (rac)-3-[(1-naphtalenyl)oxy]-1-(phenylmethyl)-pyrrolidine.

Example 11

(+)-3-[(1-Naphtalenyl)oxy]-pyrrolidine Hydrochloride (−)-3-[(1-Naphtalenyl)oxy]-pyrrolidine Hydrochloride 3-[(1-Naphtalenyl)oxy]-pyrrolidine (80 mg) was separated by preparative chiral HPLC into the separate enantiomers. Separation was performed at room temperature on a Chiracel OD column 240×4.6 mm with hexane/ethanol (80:20) and 0.15% diethylamine, flow 1 ml/minute. (+)-3-[(1-Naphtalenyl)oxy]-pyrrolidine was collected at $t_R$ 7.4 minutes, (−)-3-[(1-Naphtalenyl)oxy]-pyrrolidine was collected at $t_R$ 9.8 minutes. The solutions were immediately evaporated in vacuo and converted to their hydrochloride salts to give 10 mg of each. Estimated enantio-purity for both these enantiomers >99.5%.

TESTS

The activity of the compounds in the invention on the central nervous system was indicated using the pharmacological tests below; these tests demonstrate the serotonergic activity and antidepressant-like effects of the invention.

BINDING TESTS

The tests are carried out using cloned human receptors expressed in 3T3 cells according to the protocols described in Stam et at "Genomic organization, coding sequence and functional expression of human 5-HT2 and 5-HT1A receptor genes"—European Journal of Pharmacology—Molecular Pharmacology Section 227: 153–162 (1993) and Stam et al "Genomic organisation and functional expression of the gene encoding the human serotonin 5-HT2C receptor"—European Journal of Pharmacology—Molecular Pharmacology Section 269: 339–348 (1994). The affinity for the 5-HT2A and 5-HT2C receptors is determined by the capacity of the compounds to displace [3H]-ketanserin and [3H]-mesulergine from the appropriate receptor.

PENILE ERECTION TEST

This test, carried out according to the protocol of Berendsen et al ["Involvement of 5-HT1C receptors in drug-induced penile erections in rats"—Psychopharmacology 101: 57–61(1990)] enables the potential in vivo activity at 5HT2C receptors to be assessed.

DRL-72 TEST

This test, carried out according to the protocol of Andrews et al ["Effects of imipramine and mirtazapine on operant performance in rats"—Drug Development Research 32: 58–66 (1994)], gives an indication of potential antidepressant-like activity.

| Compound | Binding pKi | | Erection of the penis (MED, mg.kg-1) | Increase in pellets earned in DRL-72 (MED, mg.kg-1) |
|---|---|---|---|---|
| | 5HT2A | 5HT2C | | |
| 5d | 6.4 | 7.5 | 1 | 10 |
| 10b | 6.3 | 7.6 | 1 | 10 |
| 9a | 6.8 | 8 | 0.46 | 3 |

The results show that the compounds of this invention have a greater affinity for human 5-HT2C than for human 5-HT2A receptors, and that this affinity correlates with agonist activity in vivo as well as with antidepressant-like activity in an animal model for antidepressant efficacy.

What is claimed is:

1. A compound of the formula

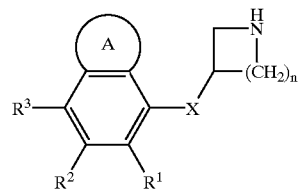

wherein A is a saturated or unsaturated, non-heterocyclic 5-membered ring;

$R^1$, $R^2$ and $R^3$ are independently H, (1–6C) alkyl, (1–6C) alkoxy, (1–6C) alkoxy-(1–6C) alkyl, carbo (1–6C) alkoxy or halogen;

X is O or S;

and n is 1 or a pharmaceutically acceptable salt thereof.

2. The compound according to claim 1, wherein R¹ is H, (1–6C) alkyl, (1–6C) alkoxy, or (1–6C) alkoxy-(1–6C) alkyl; R² is H, (1–6C) alkoxy, carbo (1–6C) alkoxy or halogen, and R³ is H, (1–6C) alkyl, (1–6C) alkoxy or halogen.

3. The compound according to claim 1 having the formula

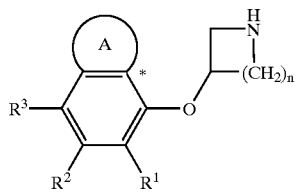

wherein A is an unsubstituted, saturated, non-heterocyclic 5-membered ring; R¹ is H or (1–6C) alkoxy; R² is H, (1–6C) alkoxy or halogen; R³ is H or halogen; and n is 1.

4. The compound of claim 3, wherein A is an unsubstituted, saturated, non-heterocyclic 5-membered ring; R¹ is (1–6C) alkoxy and R² and R³ are H.

5. The compound of claim 4, wherein A is a 5-membered ring and R¹ is methoxy.

6. A pharmaceutical composition comprising an effective amount of 3-(naphth-1-yl-oxy)-pyrrolidin or 3-(5,6,7,8-tetrahydro-naphth-1-yl-oxy)-pyrrolidin for 5-HT2C receptor agonist activity and pharmaceutically suitable auxiliaries.

7. A method for effective 5-HT2C agonist activity comprising administering an effective amount of 3-(naphth-1-yl-oxy)-pyrrolidin or 3-(5,6,7,8-tetrahydro-naphth-1-yl-oxy)-pyrrolidin to a patient in need thereof.

8. The compound of claim 1, wherein A is substituted with oxo or (1–6C) alkyl.

9. A pharmaceutical composition comprising an effective amount of the compound of claim 1 for 5-HT2C receptor agonist activity and pharmaceutically suitable auxiliaries.

10. A method for effecting 5-HT2C agonist activity in a patient comprising administering an effective amount of the compound of claim 1 to a patient in need thereof.

* * * * *